United States Patent
Meier et al.

(10) Patent No.: US 9,351,841 B2
(45) Date of Patent: May 31, 2016

(54) STRAIGHT STEM FOR THE IMPLANTATION INTO A PROXIMAL FEMUR

(75) Inventors: Rolf Meier, Winterthur (CH); Roland Baege, Wiesendangen (CH)

(73) Assignee: ZIMMER GMBH, Winterthur (CH)

( * ) Notice: Subject to any disclaimer, the term of this patent is extended or adjusted under 35 U.S.C. 154(b) by 192 days.

(21) Appl. No.: 13/981,158

(22) PCT Filed: Jan. 27, 2012

(86) PCT No.: PCT/EP2012/051328
§ 371 (c)(1),
(2), (4) Date: Sep. 20, 2013

(87) PCT Pub. No.: WO2012/101255
PCT Pub. Date: Aug. 2, 2012

(65) Prior Publication Data
US 2014/0005795 A1    Jan. 2, 2014

(30) Foreign Application Priority Data

Jan. 27, 2011    (EP) ..................................... 11000658

(51) Int. Cl.
*A61F 2/36* (2006.01)
*A61F 2/46* (2006.01)
*A61F 2/30* (2006.01)

(52) U.S. Cl.
CPC ............... *A61F 2/3662* (2013.01); *A61F 2/367* (2013.01); *A61F 2/3676* (2013.01); *A61F 2/4607* (2013.01);
(Continued)

(58) Field of Classification Search
CPC ..... A61F 2/3662; A61F 2/3676; A61F 2/367; A61F 2/3672; A61F 2002/3674; A61F 2002/3666; A61F 2002/3668; A61F 2002/3688
See application file for complete search history.

(56) References Cited

U.S. PATENT DOCUMENTS

| | | | | |
|---|---|---|---|---|
| 4,101,985 A | * | 7/1978 | Baumann | A61F 2/30739 606/67 |
| 5,888,210 A | * | 3/1999 | Draenert | 623/23.35 |
| 2011/0251697 A1 | * | 10/2011 | Chung et al. | 623/23.15 |

FOREIGN PATENT DOCUMENTS

| | | |
|---|---|---|
| DE | 2705153 A1 | 8/1978 |
| EP | 0159510 A2 | 3/1985 |

(Continued)

OTHER PUBLICATIONS

"International Application Serial No. PCT/EP2012/051328, International Preliminary Report on Patentability mailed Jan. 17, 2013", 5 pgs.

(Continued)

*Primary Examiner* — Brian Dukert
(74) *Attorney, Agent, or Firm* — Schwegman Lundberg & Woessner, P.A.

(57) ABSTRACT

The present invention relates to a straight stem (10) for the implantation into a proximal femur, the stem (10) comprising a proximal stem section (12) and a distal stem section (14), the distal stem section (14) having a distal end (24) and a distal tip (26) arranged directly adjacent to the distal end (24) and defining a distalmost point of the distal end (24), the stem (10) having, in an anterior-posterior view, a medial contour and a lateral contour, and the stem (10) having a straight stem center axis (20) between the medial contour and the lateral contour, wherein the distal end (24), in an anterior-posterior view, has a convexly curved contour, and wherein the convexly curved contour of the distal end (24) merges with straight sections (46, 48) of the medial contour and of the lateral contour at a medial merging point (22) and a lateral merging point (28), respectively, wherein the medial merging point (22) and the lateral merging point (28) are offset with respect to each other in a direction parallel to the stem center axis (20), wherein the lateral merging point (28) is arranged proximally with regard to the medial merging point (22), wherein the convexly curved contour of the distal end (24) is such that the distal tip (26) is medially offset with respect to the stem center axis (20), wherein the convexly curved contour of the distal end (24) has a curved medial section extending between the distal tip (26) and the medial merging point (22) and a curved lateral section extending between the distal tip (26) and the lateral merging point (28), and wherein the contour of the distal end (24) is asymmetrically convexly curved such that the degree of curvature of the curved lateral section is smaller than the degree of curvature of the curved medial section.

19 Claims, 5 Drawing Sheets

(52) U.S. Cl.
CPC ............... *A61F 2002/30153* (2013.01); *A61F 2002/30327* (2013.01); *A61F 2002/30574* (2013.01); *A61F 2002/30616* (2013.01); *A61F 2002/30879* (2013.01); *A61F 2002/4619* (2013.01)

(56) References Cited

FOREIGN PATENT DOCUMENTS

| EP | 0780106 | A2 | 6/1997 |
|---|---|---|---|
| FR | 2674744 | A1 | 10/1992 |
| WO | WO-2012101255 | A1 | 8/2012 |

OTHER PUBLICATIONS

"International Application Serial No. PCT/EP2012/051328, International Search Report mailed Apr. 25, 2012", 3 pgs.

"International Application Serial No. PCT/EP2012/051328, Written Opinion mailed Apr. 25, 2012", 5 pgs.

* cited by examiner

STRAIGHT STEM FOR THE IMPLANTATION INTO A PROXIMAL FEMUR

CLAIM OF PRIORITY

This patent application is a U.S. National Stage Filing under 35 U.S.C. §371 of International Patent Application Serial No. PCT/EP2012/051328, filed on Jan. 27, 2012 and published on Aug. 2, 2012 as WO 2012/101255 A1, which claims the benefit of priority of European Application Serial No. 11000658.2, filed on Jan. 27, 2011, the benefit of priority of each of which is claimed hereby and each of which is incorporated by reference herein in its entirety.

The present disclosure relates to a straight stem for the implantation into a proximal femur.

During hip replacement surgery a hip implant is generally used to replace the hip joint. During total hip arthroplasty a femoral stem is introduced into a proximal part of the femur of a patient. The recovery times are frequently long. Moreover, as a hip implant has a limited lifetime, bone conservation is an important aspect of total hip arthroplasty, particularly for younger patients. By removing as little bone as possible during a primary operation, the surgeon leaves more options for any potential future revision surgery. Moreover, it is important to reduce stresses which may arise where the implanted stem is in contact with the bone.

One object of this disclosure is therefore to provide a straight stem whose stem design helps prevent undue stresses in the bone from arising.

Generally, the present disclosure provides straight stems having an asymmetrically convexly curved contour of the distal end.

The present disclosure provides a straight stem for the implantation into a proximal femur. The stem comprises a proximal stem section and a distal stem section, the distal stem section having a distal end and a distal tip arranged directly adjacent to the distal end and defining a distalmost point of the distal end. The stem has, in an anterior-posterior view, a medial contour and a lateral contour. Further, the stem has a straight stem center axis between the medial contour and the lateral contour. The distal end of the stem, in an anterior-posterior view, has a convexly curved contour. The convexly curved contour of the distal end merges with straight sections of the medial contour and of the lateral contour at a medial merging point and a lateral merging point, respectively. The medial merging point and the lateral merging point are offset with respect to each other in a direction parallel to the stem center axis, and the lateral merging point is arranged proximally with regard to the medial merging point. The convexly curved contour of the distal end is such that the distal tip is medially offset with respect to the stem center axis. The convexly curved contour of the distal end has a curved medial section extending between the distal tip and the medial merging point and a curved lateral section extending between the distal tip and the lateral merging point, and wherein the contour of the distal end is asymmetrically convexly curved such that the degree of curvature of the curved lateral section is smaller than the degree of curvature of the curved medial section.

As is obvious to the skilled person, a high degree of curvature means a small local radius of curvature, whereas a low degree of curvature means a large local radius of curvature. Insofar the comparison of a first curved geometry having a high degree of curvature and a second curved geometry having a low degree of curvature means that the first geometry has a smaller local radius of curvature than the second geometry. An increasing degree of curvature means a decreasing local radius of curvature, and a decreasing degree of curvature means an increasing local radius of curvature. As is further obvious and well-known, any segment of a curved geometry can locally be approximated by a circular arc. The radius of this circular arc is the local radius of curvature.

An asymmetrically convexly curved contour of the distal end of the stem as disclosed herein ensures a smooth transition on the lateral contour in the region where—in the implanted state—the stem gets out of contact with the bone. Moreover, as the length of the laterally rounded portion of the distal end is relatively long, high stresses can be reduced, as less pressure is applied to that portion of the femoral bone.

As no sharp corners or other protrusions are present on the lateral contour of the stem, the forces arising under load are deflected or distributed along the lateral contour of the stem and prevent local high pressure fields from arising.

If the distal tip is medially offset with respect to the stem center axis, the distal end can be provided with an even longer lateral convex portion which ensures an improved force deflection or distribution along the lateral distal end of the stem reducing the stresses arising there.

The curved contour of the distal end of the stem as disclosed herein is of particular advantage for a straight stem. Generally, one distinguishes between straight stems, anatomical stems and curved stems. The present disclosure relates to straight stems. While the use of curved stems allows a complete preservation of the Great Trochanter, the implantation of straight stems is aimed at the longitudinal axis of the femur. Thus, only straight stems allow a clear definition of a stem center axis between the medial contour and the lateral contour of the stem. Moreover, a straight stem has a relatively long straight section on the lateral side and also on the medial side. Typically, these straight sections define a taper of the stem in a frontal view of approximately 5 to 6°, while substantially planar anterior and posterior surfaces of the stem define a taper of the stem in a lateral view of approximately 1.5 to 2°.

Providing a straight stem with a distal end which is curved as disclosed herein provides for a relatively long lateral support for the stem at the bone without the need for an excessive length of the stem or for overly strong curvatures at the distal end of the stem, and thus without the occurrence of local high pressure fields even under high loads.

In an embodiment, in a direction parallel to the stem center axis the distance between the lateral merging point and the distal tip is n-times larger than the distance between the medial merging point and the distal tip, wherein $2 \leq n \leq 10$.

A relatively long distance between the lateral merging point and the distal tip ensures a smooth lateral distal contour of the stem which contour even further reduces the stresses arising under load at the interface between the femur and the lateral contour of the implant.

In a further embodiment, in a direction perpendicular to the stem center axis and in the region of the medial merging point, the distal stem section has a width W and the distal tip is medially offset with respect to the stem center axis by a distance T, and wherein $0.25*W/2 \leq T \leq 0.75*W/2$.

These are beneficial values for ensuring the realization of a smooth lateral contour, which is advantageous in reducing the stresses arising at an interface between the stem and the femur.

In a further embodiment the curved lateral section of the distal end is defined by at least one radius of curvature R1, and wherein $100 \text{ mm} \leq R1 \leq 200 \text{ mm}$. This radius ensures an advantageously smooth transition of the straight stem up to the distal tip of the stem.

In a further embodiment the curved lateral section of the distal end has at least two curved sections with a radius of curvature R1 and R2, respectively, and wherein $5*R2 \leq R1 \leq 100*R2$. This selection is carried out to ensure an advantageously smooth lateral curved section up to the distal end tip.

In a further embodiment the curved lateral section of the distal end is defined by at least one radius of curvature R1 and the curved medial section of the distal end is defined by at least one radius of curvature R3, and wherein $10*R3 \leq R1 \leq 150*R3$. This selection of R3 is selected to generate a smooth and relatively short transition between the medial straight section and the distal end tip.

In a further embodiment the convexly curved contour of the distal end has at least two curved sections, adjacent ones of the sections of the medial and lateral contours merging at a common point, and wherein each pair of adjacent sections have a common tangent at their common point. Having a common tangent at their common point ensures smooth transitions between the adjacent contours of the stem.

In a further embodiment the degree of curvature of the distal end decreases from the lateral merging point to the medial merging point. This ensures a smooth outer contour of the distal end region of the straight stem.

In a further embodiment the proximal section comprises a connection portion for connecting a neck to the stem, the connection portion comprising a collar having, in an anterior-posterior view, a medial contour, wherein the medial contour of the stem comprises a concavely curved section extending between the straight medial section and the collar, wherein the concavely curved section of the medial contour comprises at least first and second curved sections, the first curved section merging with the straight medial section and the second curved section merging with the medial contour of the collar, and wherein the degree of curvature of the first curved section is smaller than the degree of curvature of the second curved section, in particular wherein the medial contour of the collar is convexly curved.

It has been found that the medial contour of the stem as disclosed herein permits a good insertion of the stem into the patient's femur and a good reproduction of the femur's shape even if a pronounced collar is provided at the stem for the reception of a modular femoral neck. Thus, the present disclosure enables the use of a medial contour which is ideal for reproducing the patient's anatomy and at the same time allows for a smooth transition into the collar.

In an embodiment the first and second curved sections of the medial contour have a radius of curvature Ra and Rb, respectively, wherein $5*Rb \leq Ra \leq 10*Rb$. This can provide for an advantageously smooth transition from the medial straight section up to the collar of the stem.

In a further embodiment the medial contour of the stem has at least one third curved section between the first and second curved sections, the degree of curvature of the third curved section being different from the degrees of curvature of the first and second curved sections, in particular wherein the third curved section has a radius of curvature Rc, and wherein Rb<Rc<Ra, in particular wherein $2*Rc \leq Ra \leq 5*Rc$. This third contour can provide for an even smoother transition from the medial straight section up to the collar of the stem.

In a further embodiment the stem has a lateral shoulder, the stem center axis extending between the distal end and the lateral shoulder. The straight section of the lateral contour of the stem may extend from the distal end to the lateral shoulder. In a transverse plane the cross section of the stem may have a generally rectangular shape along the stem center axis between the distal end and the lateral shoulder.

In a further embodiment the stem has an anterior surface and a posterior surface which are substantially planar at least in the distal stem section, wherein the stem tapers towards the distal end in a frontal plane as well as in a sagittal plane, the frontal plane taper being defined by the straight sections of the medial and the lateral contours of the stem, and the sagittal plane taper being defined by the planar anterior and posterior surfaces of the stem.

The different embodiments described above in accordance with the scope of the independent claims and the features realized there can naturally be combined with one another.

Further embodiments of the disclosure are also recited in the dependent claims, the description and the drawings.

Further areas of applicability of the present disclosure will become apparent from the detailed description provided hereinafter. It should be understood that the detailed description and specific examples are intended for the purpose of illustration only and are not intended to limit the scope of the disclosure in any way. The figures are simplified and schematic. Details not necessary for the understanding of the disclosure are omitted.

The present disclosure will be explained in more detail and become fully understood from the detailed description and the accompanying drawings, wherein.

All anatomical terms relating to directions or locations, such as anterior, posterior, medial, lateral, proximal and distal, refer to an implanted state of the components and implants described herein.

Figure 1A:
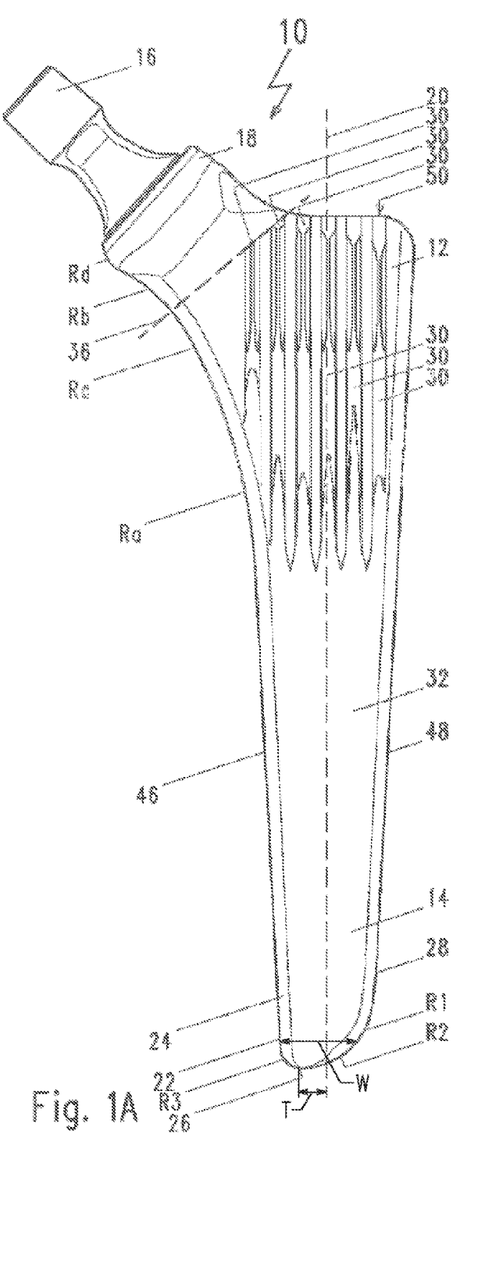
FIG. 1A shows a perspective view of an embodiment of the straight stem.

FIG. 1A shows an embodiment of a straight stem 10 having a proximal stem section 12 and a distal stem section 14. The straight stem 10 shown in FIG. 1A is of a specific size and will be described with reference to this size. Naturally speaking specific parameters used to describe this size can deviate throughout the different ranges of stem sizes used.

A medial part of the proximal stem section 12 has a modular femoral neck 16 installed on a collar 18. The modular femoral neck 16 is aligned in accordance with a patient's CCD angle relative to a stem center axis 20 following installation thereof and serves to carry a femoral head (not shown). The collar 18, also referred to as yoke, of the neck portion is dimensioned such that it can receive the modular femoral neck 16 and impart sufficient support to the modular femoral neck 16 under load.

Modular femoral necks 16 which can be introduced into the stem 10 are used, as they provide a surgeon with the ability to precisely match a wide range of male and female patient anatomies without compromise, as a high variability in femoral head height and offset has been found among patients, and the modular femoral necks 16 allow the surgeon to efficiently respond intra-operatively to excessive femoral deviations and also to discrepancies which can arise e.g. due to X-ray templating etc.

To allow a femoral stem 10 to receive a modular femoral neck 16 the collar 18 of the stem 10 has to be reinforced. For this reason the collar 18 has a generally convexly curved outer contour Rd whose medial contour merges with the concavely curved medial contour (Ra, Rc, Rb) of the proximal stem section 12.

In the above embodiment the concavely curved medial contour Ra, Rc, Rb merges with a straight stem section 46 at an intermediate region of the stem 10 which defines the transition from the proximal stem section 12 into the distal stem section 14. At a medial merging point 22 the medial straight section 46 merges into a distal end region 24 of the stem 10 having a generally convex shape R1, R2, R3.

In the present embodiment the convex shape of the distal end region 24 has a distal tip 26 as its most distal point which also defines a mathematical turning point with regard to the convexly shaped distal end region 24. The distal tip 26 is also medially offset with respect to the stem center axis 20. The convexly shaped distal end region 24 also has a curved lateral region R1, R2 which extends from the distal tip 26 up to a lateral merging point 28. The curved lateral region R1, R2 then merges with a straight section 48 of the lateral contour at the lateral merging point 28. The lateral straight stem section 48 then extends up to a stem shoulder 50 arranged at the proximal stem section 12.

The proximal stem section 12 has a plurality of ribs 30 provided on anterior and posterior surfaces 32, 34 of the stem 10 in a direction parallel to the stem center axis 20. A resection line 36 is indicated in FIG. 1A. The ribs 30 stop adjacent to the resection line 36. The resection line 36 is the line at which a hip bone (proximal femur, not shown) is resected to remove the natural femoral head from the femur and the position at which the stem 10 is implanted in its place. Naturally speaking the ribs 30 can alternatively stop short of the resection line 36 or project beyond this. The portion adjacent this resection line 36 of the stem 10 is also referred to as the femoral head region of the stem 10.

The medial contour of the proximal stem section 12 is composed of a curved section Ra, Rc, Rb merging with the medial contour Rd of the collar 18 and the straight medial section 46. As can be seen from FIG. 1A the degree of curvature of the medial contour of the stem 10 increases from the merging point between the straight medial section 46 and a first curved section Ra to the merging point between a second curved section Rb and the convexly curved contour Rd of the collar 18.

In fact the curved medial section of the example shown in FIG. 1A is best described with reference to three adjacent curved sections Ra, Rc, Rb whose respective degree of curvature decreases from the collar 18 to the medial straight section 46. Moreover, the different merging points of the different curved sections are selected such that a pair of adjacent sections have a common tangent at their common merging point.

Generally speaking the first curved section has a radius of curvature Ra which is in the range from 50 to 150 mm, in particular in the range of 80 mm to 120 mm and in the example of FIG. 1A has a radius of curvature of approximately 100 mm.

The second curved section has a radius of curvature Rb which is in the range of 5 to 25 mm, in particular in the range of 10 mm to 20 mm and in the example of FIG. 1A has a radius of curvature of approximately 15 mm.

The third curved section has a radius of curvature Rc which is in the range of 15 mm to 45 mm, in particular in the range of 20 mm to 40 mm and in the example of FIG. 1A has a radius of curvature of approximately 30 mm. The collar 18 in the example of FIG. 1A has a radius of curvature in the range of 3 mm to 25 mm, but in the context of this application is not restricted to any specific curved shape, providing it is a convexly shaped part.

Inspecting the distal stem section 14, we see that the distal tip 26 is arranged adjacent to the distal end 24 and defines a distalmost point of the distal end 24. The distal end 24 has a generally convexly curved outer contour R1, R2, R3 whose maximum lies at the distal tip 26, and whose respective curved sections merge with the medial merging point 22 and the lateral merging point 28. Again the distal end region 24 of the present example can also be described by three curved sections R1, R2, R3 which respectively merge at common merging points. Again each pair of adjacent sections has a common tangent at their merging point.

A radius of curvature R3 of the curved section extending between the medial merging point 22 and the distal tip 26 has a radius of curvature R3 which can be selected from the range of 0 to 5 mm depending on the size of the stem used and in the present example corresponds to approximately 2.2 mm. Moreover, the radius of curvature R2 of the section extending between the distal tip 26 and the third curved section R1 has a size which lies in the range of 2 to 20 mm and in the example of FIG. 1A has a size of approximately 7.1 mm. The radius of curvature R1 of the further section merging with the lateral straight section 48 can be selected in a range from 100 mm to 200 mm and in the present example of FIG. 1A is approximately 150 mm.

It is due to the lateral outer contour R1, R2 of the convexly shaped distal end 24 which ensures the reduction of the stresses following the insertion of the stem 10 into the femur. This is because the curved section better deflects or distributes peak forces arising under load.

Generally speaking the distal tip 26 is medially offset with respect to the stem center axis 20 by a distance T. The distance T is proportional to the width W of the stem 10 at the height of the medial merging point 22. The distance T may be selected according to the following relationship:

$$0.25*W/2 \leq T \leq 0.75*W/2.$$

In the present example of FIG. 1A the distance T is approximately 5 mm and the width W is approximately 18 mm.

Figure 1B:
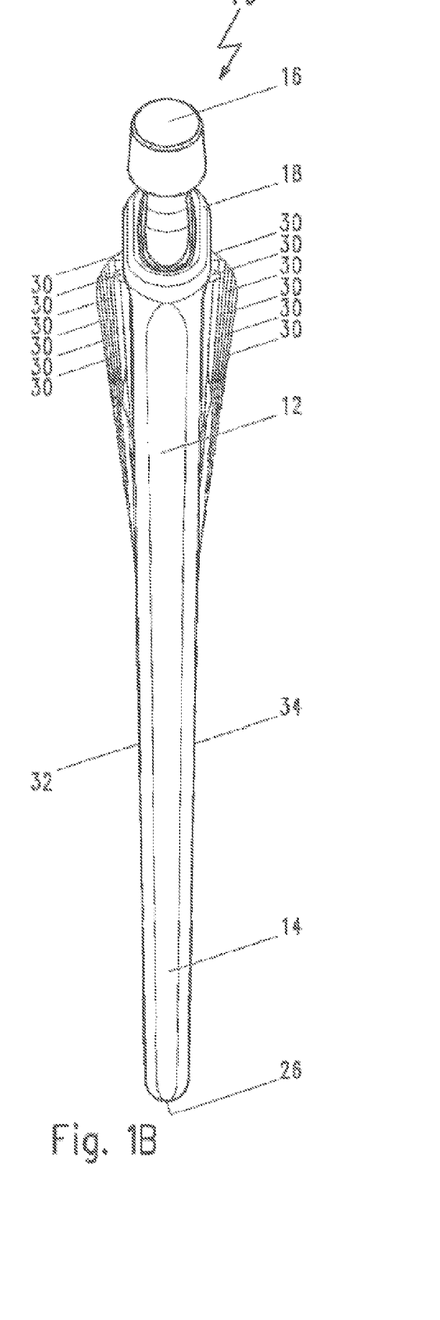
FIG. 1B shows a different perspective view of the embodiment shown in FIG. 1A.

FIG. 1B shows a medial side view of the stem of FIG. 1A. As can be seen from FIG. 1B, the anterior and posterior surfaces 32, 34 of the distal stem section 14 are generally planar. The anterior and posterior surfaces 32, 34 are also provided with ribs 30 in the proximal stem section 12.

The stem 10 generally tapers from the most proximal point of the proximal stem section 12 to the distal tip 26.

Figure 2:
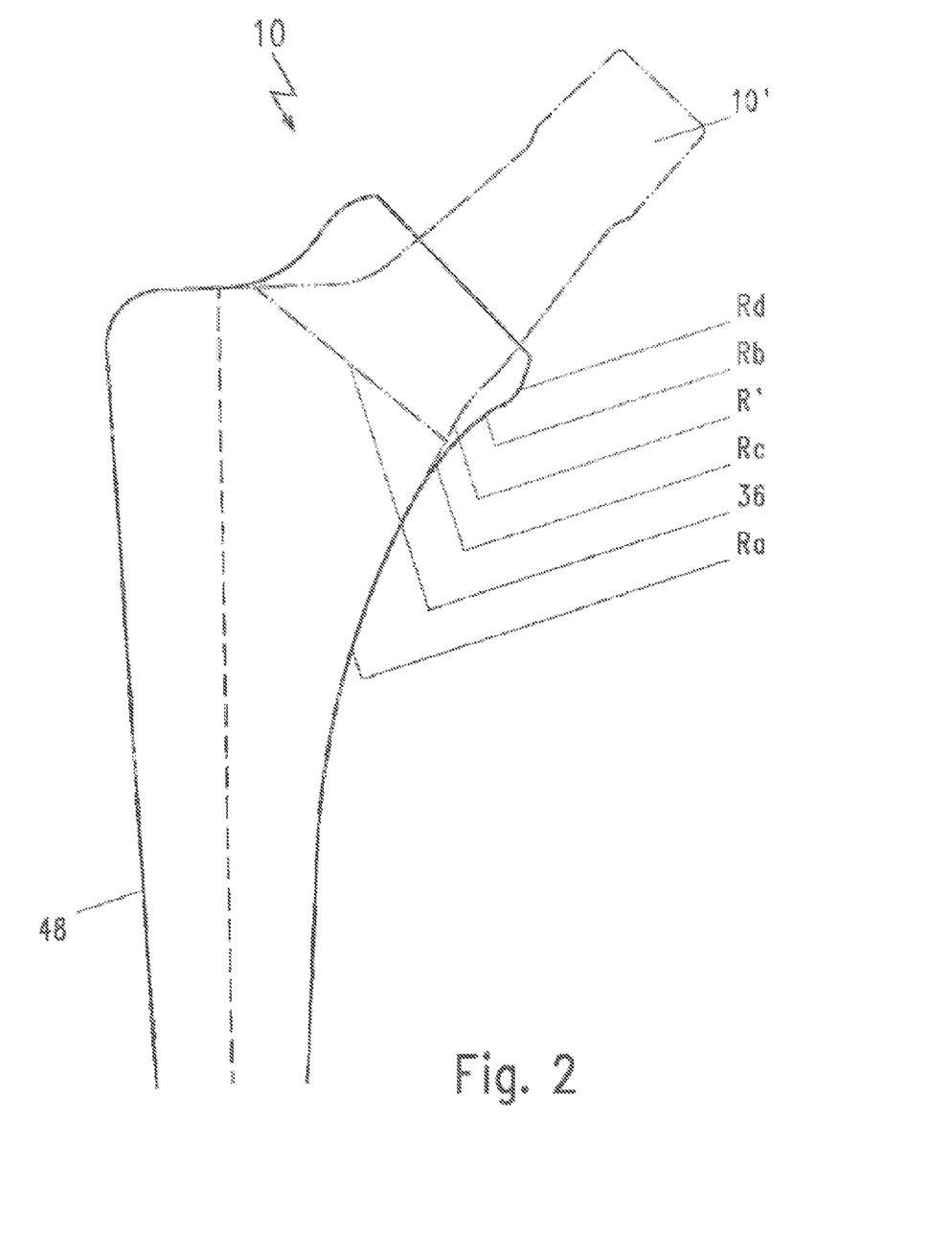
FIG. 2 shows a further embodiment of a straight stem.

FIG. 2 shows an outline of a stem 10 without a modular femoral neck 16 inserted at the collar 18 in solid lines and a comparison to a single piece prior art stem 10' indicated by the dashed lines. As is indicated by the arrows, the radius of curvature Ra, Rc, Rb of the concavely shaped medial contour is clearly different to that of the prior art one piece stem 10'.

It has surprisingly found that this larger stem body of the stem 10 still permits a good insertion into the patient's femur even though the convexly shaped collar 18 is provided. The resection line 36 is also indicated.

Figure 3A:
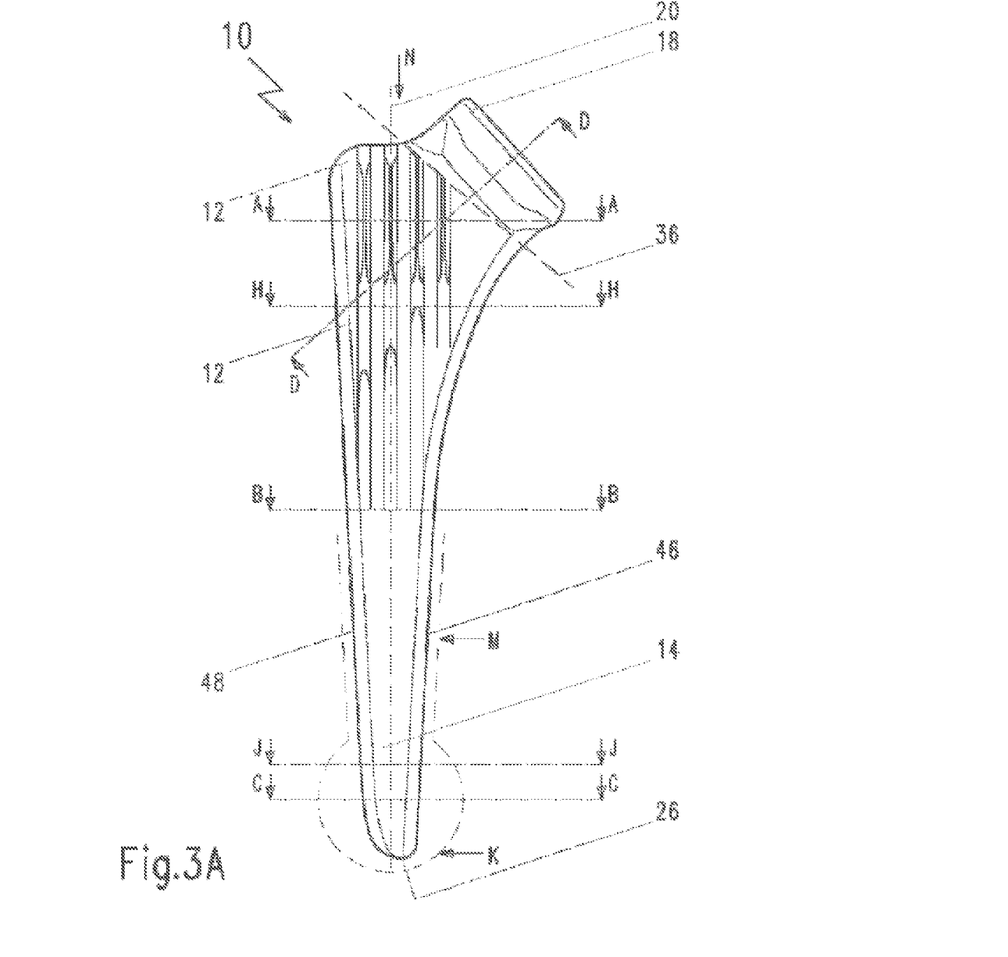
FIG. 3A shows an embodiment of a straight stem.
Figure 3B:
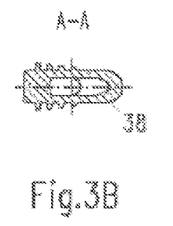
FIGS. 3B to 3J show different sectional illustrations of the embodiment shown in accordance with FIG. 3A.
Figure 3C:
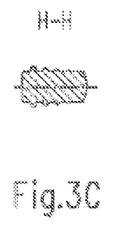
Figure 3D:
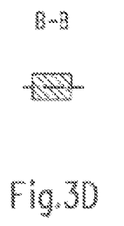
Figure 3E:
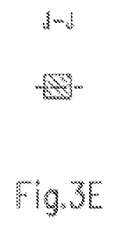
Figure 3F:
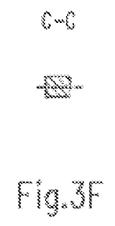

FIG. 3A shows a further embodiment of a straight stem 10. In the present example a plurality of sectional lines are indicated in the illustration of FIG. 3A. The sectional lines AA, HH, BB, GG and CC show the substantially rectangular shape of the cross-section of the stem 10 as is depicted in FIGS. 3B to 3F. The cross-sections of the proximal stem section 12 of the stem 10 shown in FIGS. 3B and 3C shows how the height of the ribs 30 increases from a lateral side of the stem 10 to a medial side of the stem 10.

Figure 3G:
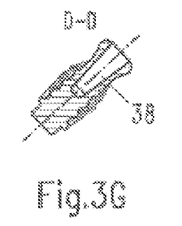

Moreover, the section along the line DD shown in FIG. 3G, clearly shows a recess 38 provided in the stem 10 for the reception of the modular femoral neck 16.

Figure 3H:
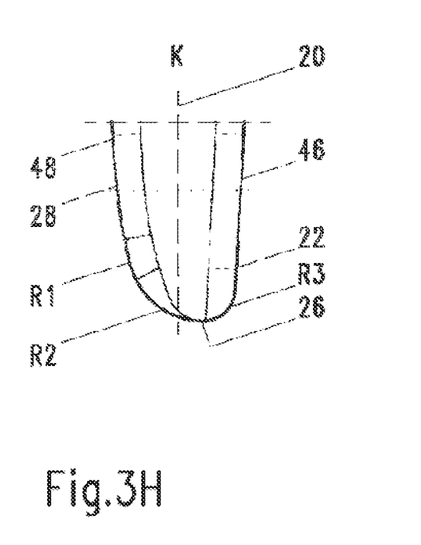

FIG. 3H shows an enhanced view of the curved distal end region 24 of the stem 10. From this drawing one can clearly see that the medial merging point 22 is far closer to the distal tip 26 than the lateral merging point 28, as measured along the stem center axis 20.

Thus, the asymmetry of the contour of the distal end 24 is in this example due to the medial offset of the distal tip 26 with respect to the stem center axis 20 and the proximal offset of the lateral merging point 28 with respect to the medial merging point 22. In other embodiments not presented here, only one of these offsets may be provided without leaving the scope of the present disclosure.

Figure 3I:
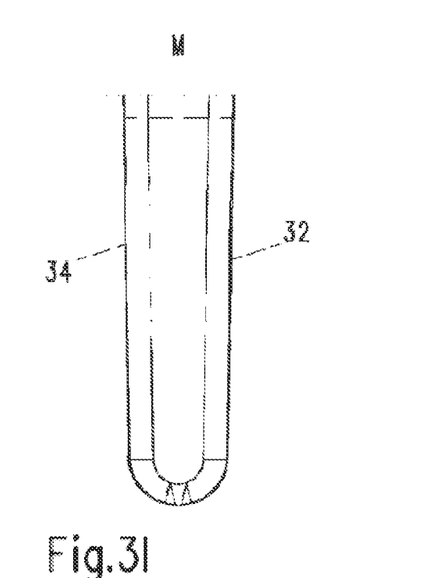

FIG. 3I shows a view onto the stem 10 in the direction M of 3A and shows the generally planar surfaces of the posterior and anterior surfaces of the distal region of the stem of FIG. 3A.

Figure 3J:
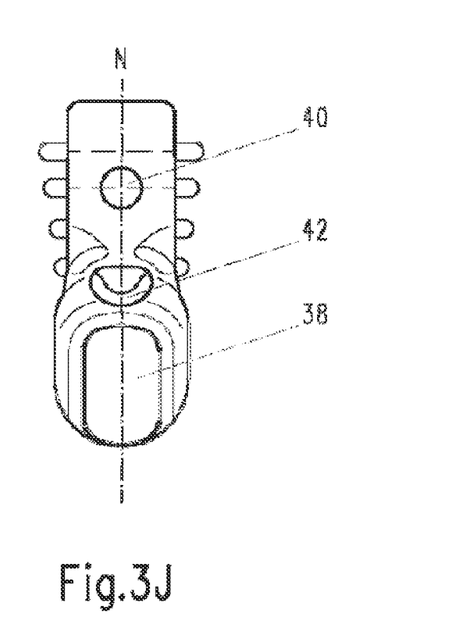

FIG. 3J shows a view onto the proximal top side of the stem 10 in the direction N of FIG. 3A. A recess 40 for a stem extractor (not shown) is provided. Moreover, the recess 38 for inserting the modular femoral neck 16 can also be seen. At the end of the stem 10 is a small hole 42 which is generally the interface to an impaction instrument (not shown), i.e. the tool which is used for the insertion of the modular femoral head 16.

Generally speaking the stem 10 has a proximal primary fixation which is achieved by a press fit of the stem 10 in the femur. The general cross-section of the stem 10 can best be described as being primarily rectangular, and increasing sizes of stems 10 are wider in the medial-lateral direction than in the proximal-distal direction and are all based on an at least similar medial curved contour Ra, Rc, Rb. The number of ribs 30 and the anterior-posterior width also increases with an increase in size of these stems 10. The stem 10 is generally intended to be used for cement-less implant for total hip arthroplasty.

Figure 4:
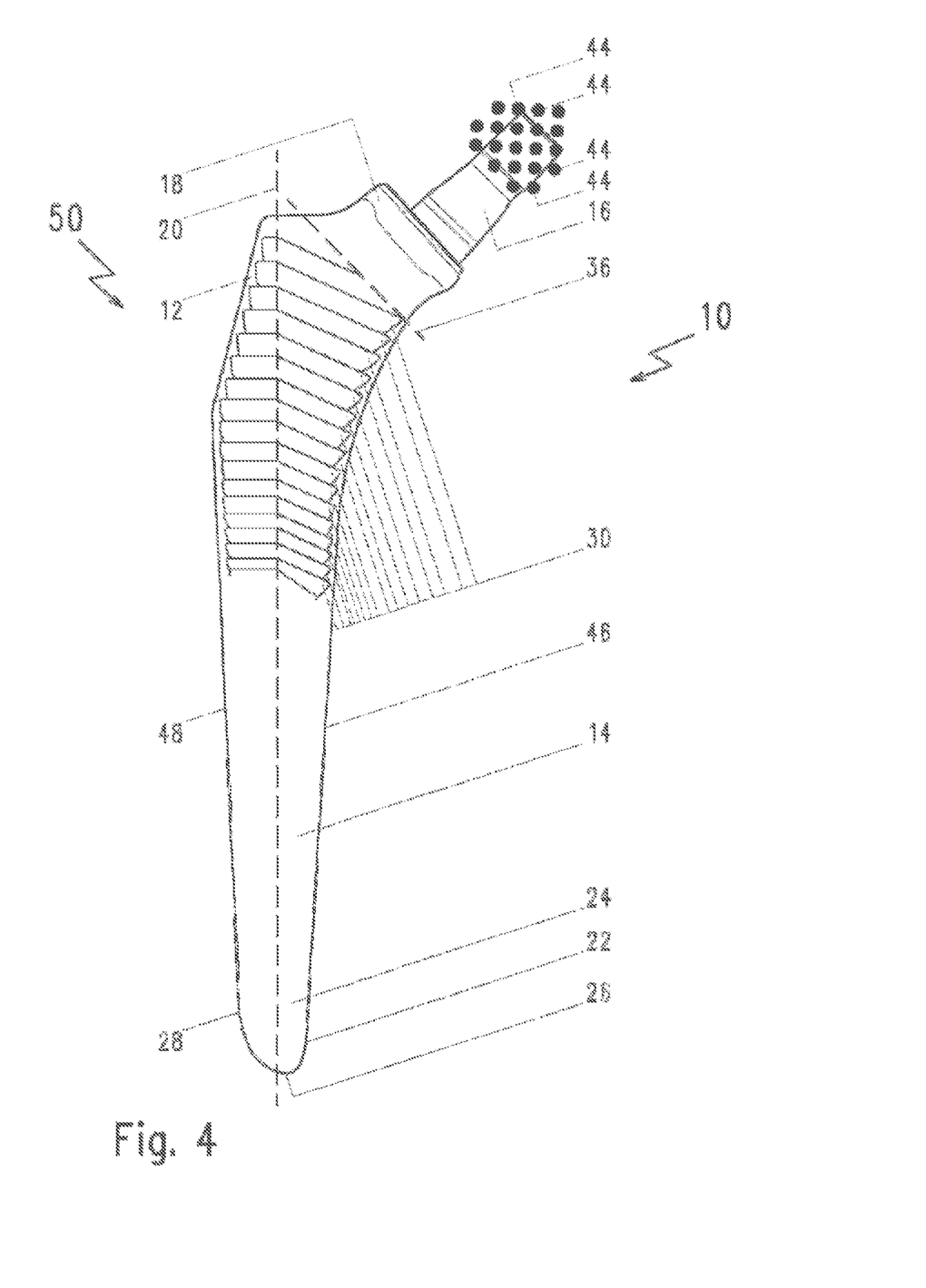
FIG. 4 shows a further embodiment of a straight stem.

FIG. 4 shows a further embodiment of a straight stem 10. In the example of FIG. 4 the ribs 30 are aligned generally perpendicular to the stem center axis 20. Generally speaking the alignment of the ribs 30 can be selected at random.

FIG. 4 also shows how a straight stem 10 can be realized with a shoulder portion 50 which is less pronounced when compared to the shoulder portion of the stem 10 depicted in FIGS. 1A to 3J. Adjacent the modular femoral neck 16 are a series of dots 44. These dots 44 indicate a typical variation of the position of a femoral head (not shown) which indicates the flexibility a surgeon has when using the modular femoral neck 16 in combination with the stem 10 presented here.

The present disclosure also refers to a set of straight stems as disclosed herein having different sizes, wherein at least a plurality of differently sized stems within the set have the same degree of curvature, in particular the same radius of curvature, for their convexly curved lateral section R1 of the distal end 24, in particular R1 being at least approximately 150 mm, and/or for their concavely curved medial section Ra of the medial contour of the stem, in particular Ra being at least approximately 100 mm.

The description of the disclosure is merely exemplary in nature, and, thus, variations do not depart in the gist of the disclosure are intended to be within the scope of the disclosure. Such variations are not to be regarded as a departure from the spirit in the scope of the disclosure.

LIST OF REFERENCE NUMERALS 10 straight stem
12 proximal stem section
14 distal stem section
16 modular femoral neck
18 collar
20 stem center axis
22 medial merging point
24 distal end
26 distal tip
28 lateral merging point
30 ribs
32 anterior surface
34 posterior surface
36 resection line
38 recess
40 recess
42 hole
44 dots
46 medial straight section
48 lateral straight section
50 shoulder
R1 to R3 distal contour of distal end region
Ra to Rd medial contour of stem
T distance
W width

The invention claimed is:

1. A stem for implantation into a proximal portion of a femur, the stem comprising:
 a body extending from a proximal stem section to a distal stem section,
 the body having a medial side and a lateral side and defining a straight stem center axis positioned between the medial side and the lateral side,
 the body having a cross-sectional contour, when implanted and viewed in a coronal plane, extending along the lateral side, around a distal end of the body, to the medial side,
 the contour including a lateral straight section that extends distally to a lateral merging point,
 the contour including a convexly curved lateral distal section that is devoid of straight sections and extends distally from the lateral merging point to a distal tip, the distal tip representing the distal most point of the distal end and being medially offset with respect to the stem center axis, the convexly curved lateral distal including a first region directly adjacent to the lateral merging point, the first region having a first radius of curvature, the convexly curved lateral distal section further including a second region directly adjacent to the first region, the second region having a second radius of curvature different from the first radius of curvature,
 the contour including a convexly curved medial distal section that extends proximally from the distal tip to a medial merging point, the medial merging point located more distal than the lateral merging point, and
 the contour including a medial straight section that extends proximally from the medial merging point.

2. The stem of claim 1, wherein the convexly curved medial distal section is devoid of straight sections.

3. The stem of claim 1, wherein the convexly curved lateral distal section and the convexly curved medial distal section include regions having different curvatures.

4. The stem of claim 1, wherein the convexly curved medial distal section is more steeply curved than the convexly curved lateral distal section.

5. The stem of claim 1, wherein the second radius of curvature is less than the first radius of curvature.

6. The stem of claim 1, wherein the first radius of curvature is between 100 mm and 200 mm, inclusive.

7. The stem of claim 1, wherein the first radius of curvature is between ten times the second radius of curvature and one hundred times the second radius of curvature, inclusive.

8. The stem of claim 1, wherein the convexly curved medial distal section comprises a third region directly adjacent to the second region, the third region having a third radius of curvature different from the second radius of curvature.

9. The stem of claim 8, wherein the third radius of curvature is less than the second radius of curvature.

10. The stem of claim 9, wherein the first radius of curvature is between ten times the third radius of curvature and one hundred fifty times the third radius of curvature, inclusive.

11. The stem of claim 1, wherein the contour includes common tangents at the points between adjacent sections having different curvatures.

12. The stem of claim 1, wherein, in a direction parallel to the stem center axis, the distance between the lateral merging point and the distal tip is between two and ten times larger than the distance between the medial merging point and the distal tip, inclusive.

13. The stem of claim 1,
wherein, in a direction perpendicular to the stem center axis and in the region of the medial merging point, the distal stem section has a width W and the distal tip is medially offset with respect to the stem center axis by a distance T; and
wherein $0.25 * W / 2 < T < 0.75 * W / 2$.

14. The stem of claim 1,
wherein the contour extends proximally from the medial straight section to a concavely curved section;
wherein the concavely curved section includes a first section, directly adjacent to the medial straight section, having a first radius of curvature; and
wherein the concavely curved section further includes a second section having a second radius of curvature different from the first radius of curvature.

15. The stem of claim 14, wherein the second radius of curvature is between five and ten times the first radius of curvature, inclusive.

16. The stem of claim 14, wherein the concavely curved section further includes a third section disposed between the first and second sections, the third section having a third radius of curvature greater than the second radius of curvature and less than the first radius of curvature.

17. The stem of claim 14, wherein the contour extends proximally from the second section of the concavely curved section to a collar, the collar configured to connect a neck to the stem and having a convex cross-sectional contour when implanted and viewed in the coronal plane.

18. A stem for the implantation into a proximal portion of a femur, the stem comprising:
a body extending from a proximal stem section to a distal stem section,
the body having a medial side and a lateral side and defining a straight stem center axis positioned between the medial side and the lateral side,
the body having a cross-sectional contour, when implanted and viewed in a coronal plane, extending along the lateral side, around a distal end of the body, to the medial side,
the contour including a lateral straight section that extends distally to a lateral merging point,
the contour including a convexly curved lateral distal section that extends distally from the lateral merging point to a distal tip, the distal tip representing the distal most point of the distal end and being medially offset with respect to the stem center axis, the convexly curved lateral distal section including a first region directly adjacent to the lateral merging point, the first region having a first radius of curvature, the convexly curved lateral distal section further including a second region directly adjacent to the first region, the second region having a second radius of curvature less than the first radius of curvature,
the contour including a convexly curved medial distal section that extends proximally from the distal tip to a medial merging point, the medial merging point being located more distal than the lateral merging point, the convexly curved medial distal section including a third region directly adjacent to the second region, the third region having a third radius of curvature less than the second radius of curvature,
the contour including a medial straight section that extends proximally from the medial merging point, and
wherein the contour is devoid of straight sections between the lateral merging point and the medial merging point.

19. The stem of claim 18,
wherein the first radius of curvature is between 100 mm and 200 mm, inclusive;
wherein the first radius of curvature is between ten times the second radius of curvature and one hundred times the second radius of curvature, inclusive; and
wherein the first radius of curvature is between ten times the third radius of curvature and one hundred fifty times the third radius of curvature, inclusive.

* * * * *